United States Patent
Fukuchi et al.

(10) Patent No.: US 11,192,838 B2
(45) Date of Patent: Dec. 7, 2021

(54) PRODUCTION METHOD FOR HEXAFLUORO-1,3-BUTADIENE

(71) Applicant: SHOWA DENKO K.K., Tokyo (JP)

(72) Inventors: Yohsuke Fukuchi, Tokyo (JP); Atsushi Nakamura, Tokyo (JP); Nozomi Inoue, Tokyo (JP); Mitsuhiro Hino, Tokyo (JP); Tomoki Sekiguchi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 101 days.

(21) Appl. No.: 16/611,879

(22) PCT Filed: Apr. 25, 2018

(86) PCT No.: PCT/JP2018/016881
§ 371 (c)(1),
(2) Date: Nov. 8, 2019

(87) PCT Pub. No.: WO2018/216426
PCT Pub. Date: Nov. 29, 2018

(65) Prior Publication Data
US 2021/0163382 A1 Jun. 3, 2021

(30) Foreign Application Priority Data
May 22, 2017 (JP) .............................. JP2017-101063

(51) Int. Cl.
*C07C 17/23* (2006.01)
*C07C 17/383* (2006.01)
*C07C 21/18* (2006.01)
*C07C 21/20* (2006.01)
*B01J 23/06* (2006.01)

(52) U.S. Cl.
CPC ............... *C07C 17/23* (2013.01); *B01J 23/06* (2013.01); *C07C 17/383* (2013.01); *C07C 21/18* (2013.01); *C07C 21/20* (2013.01)

(58) Field of Classification Search
None
See application file for complete search history.

(56) References Cited

U.S. PATENT DOCUMENTS

| | | | |
|---|---|---|---|
| 2006/0252968 A1 | 11/2006 | Wlassics et al. | |
| 2009/0216053 A1 | 8/2009 | Ohno et al. | |
| 2010/0280291 A1 | 11/2010 | Tortelli et al. | |

FOREIGN PATENT DOCUMENTS

| | | | |
|---|---|---|---|
| CN | 101432253 A | 5/2009 | |
| CN | 103373896 A | 10/2013 | |
| CN | 104529696 A | 4/2015 | |
| GB | 798407 A | 7/1958 | |
| JP | 54-115698 A | 9/1979 | |
| JP | 2006-312637 A | 11/2006 | |
| JP | 2007-332050 A | 12/2007 | |
| JP | 5005681 B2 | 8/2012 | |
| RU | 2359951 C1 | 6/2009 | |
| WO | 2005/023734 A1 | 3/2005 | |
| WO | 2007/125972 A1 | 11/2007 | |

OTHER PUBLICATIONS

Patent No. RU2359951, English translation, Jun. 27, 2007, pp. 1-4 (Year: 2007).*
International Preliminary Report on Patentability with English Translation of Written Opinion of the International Searching Authority for PCT/JP2018/016881 dated Nov. 26, 2019.
International Search Report for PCT/JP2018/016881, dated Jul. 24, 2018.
Extended European Search Report dated May 29, 2020, from the European Patent Office in Application No. 18805125.4.

* cited by examiner

*Primary Examiner* — Medhanit W Bahta
(74) *Attorney, Agent, or Firm* — Sughrue Mion, PLLC

(57) ABSTRACT

Provided is a method that is for producing hexafluoro-1,3-butadiene, discharges small amounts of industrial wastes, and is industrially applicable. The method for producing hexafluoro-1,3-butadiene includes a reaction step of reacting a halogenated butane represented by chemical formula, $CF_2X^1\text{-}CFX^2\text{-}CFX^3\text{-}CF_2X^4$ ($X^1$, $X^2$, $X^3$, and $X^4$ are each independently a halogen atom other than a fluorine atom) in an organic solvent in the presence of zinc to eliminate the halogen atoms, $X^1$, $X^2$, $X^3$, and $X^4$, other than the fluorine atoms to generate hexafluoro-1,3-butadiene, giving a reaction product containing the hexafluoro-1,3-butadiene, and an aftertreatment step of separating the hexafluoro-1,3-butadiene from the reaction product produced in the reaction step, then adding water to a reaction product residue after the separating, and removing the organic solvent, giving an aqueous solution of zinc halide.

12 Claims, No Drawings

PRODUCTION METHOD FOR HEXAFLUORO-1,3-BUTADIENE

CROSS REFERENCE TO RELATED APPLICATIONS

This application is a National Stage of International Application No. PCT/JP2018/016881 filed Apr. 25, 2018, claiming priority based on Japanese Patent Application No. 2017-101063 filed May 22, 2017.

TECHNICAL FIELD

The present invention relates to a method for producing hexafluoro-1,3-butadiene.

BACKGROUND ART

Hexafluoro-1,3-butadiene is useful, for example, as an etching gas for semiconductors. As the production method for hexafluoro-1,3-butadiene, various methods have been known. For example, PTL 1 discloses a method of subjecting 1,2,3,4-tetrachlorohexafluorobutane to dechlorination reaction in dioxane in the presence of magnesium at −78° C. PTL 2 discloses a method of subjecting 1,2,3,4-tetrachlorohexafluorobutane to dechlorination reaction in 2-propanol in the presence of zinc.

CITATION LIST

Patent Literatures

PTL 1: WO 2005/23734
PTL 2: JP 5005681 B

SUMMARY OF INVENTION

Technical Problem

The methods disclosed in PTLs 1 and 2, however, have a problem that, after the reaction, a large amount of a mixture of an organic solvent (dioxane, 2-propanol), a metal salt (magnesium chloride, zinc chloride), and an unreacted compound is formed, resulting in industrial wastes. Hence, the methods disclosed in PTLs 1 and 2 are unsuitable for industrial production methods for hexafluoro-1,3-butadiene. The present invention is intended to provide a method that is for producing hexafluoro-1,3-butadiene, discharges small amounts of industrial wastes, and is industrially applicable.

Solution to Problem

To solve the problems, aspects of the present invention are the following [1] to [6].

[1] A method for producing hexafluoro-1,3-butadiene includes
a reaction step of reacting a halogenated butane represented by chemical formula, $CF_2X^1$-$CFX^2$-$CFX^3$-$CF_2X^4$ ($X^1$, $X^2$, $X^3$, and $X^4$ are each independently a halogen atom other than a fluorine atom) in an organic solvent in the presence of zinc to eliminate the halogen atoms, $X^1$, $X^2$, $X^3$, and $X^3$, other than the fluorine atoms to generate hexafluoro-1,3-butadiene, giving a reaction product containing the hexafluoro-1,3-butadiene, and
an aftertreatment step of separating the hexafluoro-1,3-butadiene from the reaction product produced in the reaction step, then adding water to a reaction product residue after the separating, and removing the organic solvent, giving an aqueous solution of zinc halide.

[2] In the method for producing hexafluoro-1,3-butadiene according to the aspect [1], the organic solvent is an alcohol.

[3] In the method for producing hexafluoro-1,3-butadiene according to the aspect [2], the alcohol is at least one of methanol, ethanol, 1-propanol, and 2-propanol.

[4] The method for producing hexafluoro-3,3-butadiene according to any one of the aspects [1] to [3] further includes a neutralization step of bringing the hexafluoro-1,3-butadiene separated from the reaction product produced in the reaction step into contact with an alkali, and a water removal step of removing water from the hexafluoro-1,3-butadiene that has been brought into contact with the alkali in the neutralization step.

[5] The method for producing hexafluoro-1,3-butadiene according to the aspect [4] further includes a purification step of distilling the hexafluoro-1,3-butadiene from which water has been removed in the water removal step, by using at least two distillation columns to purify the hexafluoro-1,3-butadiene.

[6] In the method for producing hexafluoro-1,3-butadiene according to any one of the aspects [1] to [5], in the aftertreatment step, a hydrogen halide is added together with the water to the reaction product residue.

Advantageous Effects of Invention

The method for producing hexafluoro-1,3-butadiene according to the present invention discharges small amounts of industrial wastes and is industrially applicable.

DESCRIPTION OF EMBODIMENTS

An embodiment of the present invention will now be described. The present embodiment is merely an example of the present invention, and the present invention is not limited to the present embodiment. Various modifications or improvements can be made in the present embodiment, and such various modifications and improvements can be encompassed by the present invention.

A method for producing hexafluoro-1,3-butadiene of the embodiment includes a reaction step of reacting a halogenated butane represented by chemical formula, $CF_2X^1$-$CFX^2$-$CFX^3$-$CF_2X^4$ ($X^1$, $X^2$, $X^3$, and $X^4$ are each independently a halogen atom other than a fluorine atom) in an organic solvent in the presence of zinc to eliminate the halogen atoms, $X^1$, $X^2$, $X^3$, and $X^4$, other than the fluorine atoms to generate hexafluoro-1,3-butadiene, giving a reaction product containing hexafluoro-1,3-butadiene, and an aftertreatment step of separating the hexafluoro-1,3-butadiene from the reaction product produced in the reaction step, then adding water to a reaction product residue after the separating, and removing the organic solvent, giving an aqueous solution of zinc halide.

By such a method for producing hexafluoro-1,3-butadiene of the embodiment, an organic solvent and a zinc halide can be recovered in the aftertreatment step, and thus the method discharges small amounts of industrial wastes and is industrially applicable. In addition, an industrially valuable, highly pure, aqueous solution of zinc halide can be obtained. Moreover, hexafluoro-1,3-butadiene can be produced safely and inexpensively. In the present invention, "hexafluoro-1,3-butadiene" means "1,1,2,3,4,4-hexafluoro-1,3-butadiene".

Hereinafter, the method for producing hexafluoro-1,3-butadiene of the embodiment will be described in further detail. First, the reaction step will be described.

Reaction Step

The halogenated butane represented by chemical formula, $CF_2X^1\text{-}CFX^2\text{-}CFX^3\text{-}CF_2X^4$, may be any type, and $X^1$, $X^2$, $X^3$, and $X^4$ are each independently a halogen atom other than a fluorine atom and may be any of chlorine, bromine, and iodine. All of $X^1$, $X^2$, $X^3$, and $X^4$ may be the same halogen atom, or some may be the same, and the others may be different halogen atoms. For example, 1,2,3,4-tetrachloro-hexafluorobutane in which $X^1$, $X^2$, $X^3$, and $X^4$ are each chlorine can be used as the halogenated butane. In the present invention, "1,2,3,4-tetrachlorohexafluorobutane" means "1,2,3,4-tetrachloro-1,1,2,3,4,4-hexafluorobutane".

The organic solvent used in the reaction step may be any type that does not interfere with the progress of dehalogenation reaction that eliminates halogen atoms other than a fluorine atom from a halogenated butane to give hexafluoro-1,3-butadiene. For example, an alcohol, acyclic ether, an aromatic hydrocarbon, an amide solvent, an organic acid, or a mixed solvent of them can be used.

Examples of the cyclic ether include tetrahydrofuran and dioxane. Examples of the aromatic hydrocarbon include benzene and toluene. Examples of the amide solvent include N,N-dimethylformamide. Examples of the organic acid include acetic acid. Of these organic solvents, an alcohol appropriately helps the dehalogenation reaction to proceed and is preferred in the after treatment step as described later. The alcohol may be any type, and, for example, at least one of methanol, ethanol, 1-propanol, and 2-propanol can be used.

In the reaction step, the mass ratio of the zinc used to the organic solvent used ([amount of zinc]/[amount of organic solvent]) may be in a range of 0.2 or more and 2.0 or less.

The shape of the zinc is not specifically limited as long as the dehalogenation reaction proceeds, but is preferably in a powder form or a ribbon form, and is more preferably in a powder form from the viewpoint of reactivity or handling properties. A powder zinc preferably has an average particle diameter of 0.04 mm or more and 10.0 mm or less.

In the reaction step, for example, zinc and an organic solvent can be mixed, and a halogenated butane can be gradually added typically at a temperature of 20° C. or more and 150° C. or less, preferably 30° C. or more and 95° C. or less, while the pressure is typically maintained at 0.05 MPa or more and 1 MPa or less. This operation enables the dehalogenation reaction of eliminating halogen atoms other than a fluorine atom from the halogenated butane to generate hexafluoro-1,3-butadiene.

The mass ratio of the halogenated butane used to the zinc used ([amount of halogenated butane]/[amount of zinc]) may be in a range of 1 or more and 12 or less.

The reaction product containing hexafluoro-1,3-butadiene produced in the reaction step may be introduced, for example, to a distillation column, and the hexafluoro-1,3-butadiene may be gasified in the distillation column to separate a liquid phase mainly containing an organic solvent from a gas phase mainly containing the hexafluoro-1,3-butadiene. The liquid phase contains an unreacted material and by-products together with the organic solvent.

Neutralization Step

In the method for producing hexafluoro-1,3-butadiene of the embodiment, in order to remove hydrogen fluoride as a by-product contained in the hexafluoro-1,3-butadiene separated from the reaction product, the hexafluoro-1,3-butadiene separated from the reaction product may be brought into contact with an alkali to be neutralized (neutralization step). The neutralization stop is preferably performed as follows: for example, the reaction product is introduced to a distillation column to separate the hexafluoro-1,3-butadiene as a gas phase; and then the separated gas phase is brought into contact with an alkali. The neutralization step is preferably performed in a temperature condition of –15° C. or more and 60° C. or less.

The alkali may be any type, and examples include aqueous alkali solutions such as an aqueous sodium hydroxide solution and an aqueous potassium hydroxide solution. Alternatively, a solid alkali may be used. Examples of the solid alkali include refining agents containing an alkali compound such as an alkali metal compound and an alkaline earth metal compound and a support such as a carbonaceous solid material, alumina, and zeolite and a commonly used soda lime. The separated gas phase can be brought into contact with the alkali, for example, by gas bubbling of the gas phase in the aqueous alkali solution.

Water Removal Step

In the method for producing hexafluoro-1,3-butadiene of the embodiment, the hexafluoro-1,3-butadiene that has been brought into contact with the alkali in the neutralization step may be subjected to a water removal treatment (water removal step). The hexafluoro-1,3-butadiene after the neutralization step contains water, and thus the water removal step is preferably performed subsequent to the neutralization step to remove water from the hexafluoro-1,3-butadiene. The hexafluoro-1,3-butadiene that has been brought into contact with the alkali in the neutralization step may contain intermediates of the dehalogenation reaction in addition to the water.

The water removal method is not specifically limited, and a water removal treatment by contact with zeolite may be performed. Specific examples of the zeolite include molecular sieves 3A, 4A, and 5A. The water removal treatment is preferably performed in a temperature condition of –15° C. or more and 60° C. or less. The water removal treatment may be performed in a gas state or a liquid state but is preferably performed in a liquid state. The water removal step is preferably performed in a switching system including two or more lines.

Purification Step

The method for producing hexafluoro-1,3-butadiene of the embodiment may further include a purification step of distilling the hexafluoro-1,3-butadiene from which water has been removed in the water removal stop, by using at least two distillation columns to purify the hexafluoro-1,3-butadiene. The hexafluoro-1,3-butadiene from which water has been removed in the water removal step can contain an unreacted halogenated butane or intermediates of the dehalogenation reaction.

In an example of the purification step, first, the hexafluoro-1,3-butadiene from which water has been removed in the water removal step is introduced to a first distillation column, for example, by using a pump or a compressor. From the first distillation column, low-boiling components (for example, air, carbon monoxide, carbon dioxide) are extracted as the overhead distillate. As the bottom distillate, hexafluoro-1,3-butadiene is mainly extracted and is introduced to a second distillation column.

Next, from the second distillation column, a purified hexafluoro-1,3-butadiene, the target compound, is extracted as the overhead distillate and is collected as a product. Meanwhile, as the bottom distillate of the second distillation column, high-boiling components (for example, a small amount of an organic solvent, intermediates of the dehalogenation reaction) are extracted. At least a part of the high-boiling components may be returned to the reaction step.

In another example of the purification step, first, the hexafluoro-1,3-butadiene from which water has been removed in the water removal step is introduced to a first distillation column. From the first distillation column, low-boiling components and hexafluoro-1,3-butadiene are extracted as the overhead distillate. As the bottom distillate, the high-boiling components described above are extracted. At least a part of the high-boiling components may be returned to the reaction stop.

Next, the mixture of the low-boiling components and the hexafluoro-1,3-butadiene extracted from the head of the first distillation column is introduced to a second distillation column. From the second distillation column, the low-boiling components (for example, air, carbon monoxide, carbon dioxide) are extracted as the overhead distillate. Meanwhile, as the bottom distillate from the second distillation column, a purified hexafluoro-1,3-butadiene, the target compound, is extracted and is collected as a product.

Aftertreatment Step

Next, the aftertreatment step will be described. The aftertreatment step is a step of separating the hexafluoro-1,3-butadiene from the reaction product produced in the reaction step, then adding water to a reaction product residue after the separating, and removing the organic solvent to give an aqueous solution of zinc halide. The reaction product residue after the separation of the hexafluoro-1,3-butadiene may be introduced, for example, to a metal reaction container coated with Teflon (registered trademark), and water may be added.

The mass ratio of the reaction product residue to the water ([amount of reaction product residue]/[amount of water]) may be in a range of 0.5 or more and 2.0 or less. As the water, tap water, ion-exchanged water, distilled water, pure water, ultrapure water, or the like can be used, and pure water or ultrapure water is preferred.

In the aftertreatment step, an inorganic acid such as a hydrogen halide may be added together with water, as needed. A hydrogen halide reacts with unreacted zinc to convert the zinc into a zinc ion and thus improves the yield of a zinc halide. Examples of the hydrogen halide include hydrogen fluoride, hydrogen chloride, hydrogen bromide, and hydrogen iodide. For example, in order to give an aqueous zinc chloride solution in the aftertreatment step, hydrochloric acid is suitably added as the inorganic acid. The concentration of hydrochloric acid is not specifically limited and is preferably 1.0% by mass or more and 37.0% by mass or less.

When a solution obtained by addition of water to the reaction product residue in the aftertreatment step contains solid substances, solid-liquid separation may be performed. The solid-liquid separation may be performed by any method, which can be selected from settling/floating, filtration, centrifugation, and the like. Of the above methods, filtration is a simple method and thus is suitably used.

Next, from the solution after solid-liquid separation, the organic solvent is removed. The organic solvent may be removed by any method, and distillation is preferred. The distillation may be any type, which can be selected from atmospheric distillation, vacuum distillation, molecular distillation, and the like. As the atmospheric distillation, a known method including simple distillation and distillation using a distillation column with trays, such as an Oldershaw column, can be used. As the vacuum distillation, typical vacuum distillation and vacuum distillation using a rotary evaporator can be used.

In order to efficiently remove the organic solvent from the solution obtained by addition of water to the reaction product residue in the aftertreatment step, the organic solvent is preferably an alcohol, more preferably at least one of methanol, ethanol, 1-propanol, and 2-propanol, and even more preferably 2-propanol. These alcohols can be simply removed by distillation from the solution obtained by addition of water to the reaction product residue in the aftertreatment step.

By collecting the residue after removal of the organic solvent, an aqueous solution of zinc halide can be recovered as a product. The aqueous solution of zinc halide has high purity and is industrially valuable. When a resulting aqueous solution of zinc halide is colored, the aqueous solution of zinc halide may be brought into contact with a refining agent to remove the color. Examples of the refining agent include carbonaceous solid materials typified by activated carbon, zeolite, activated alumina, and silica gel, and activated carbon is preferred.

EXAMPLES

The present invention will next be described in further detail with reference to examples and comparative examples.

Example 1

Reaction Step

In an SUS316 autoclave having an internal volume of 500 ml, 119 g of 2-propanol as an organic solvent and 82.4 g of granular metal zinc were placed. The autoclave had a jacket with a cooling structure and a stirrer at the upper part, and the heating system was a jacket heating system.

While the content in the autoclave was stirred, the temperature was increased to 70° C. While the content in the autoclave was maintained at a temperature of 70° C. under normal pressure, 149 g of 1,2,3,4-tetrachlorohexafluorobutane was added dropwise at a drop rate of 9.31 g per hour and was reacted for 5 hours. After completion of the reaction for 5 hours, the reaction product was further heated to vaporize a part of the organic solvent (2-propanol) and the product, and the vapor of them was cooled, liquified, and collected. The obtained liquid was subjected to simple distillation (first distillation system), and a gas phase mainly containing the product was separated from a liquid phase mainly containing the organic solvent. The separated product was analyzed by gas chromatography to show 94.5% by volume of hexafluoro-1,3-butadiene and 5.5% by volume of other components.

Water Removal Step, Purification Step

Through a neutralization step in the condition of bubbling in an aqueous potassium hydroxide solution, the product was subjected to a water removal treatment with molecular sieves in a temperature condition of 0° C., then high-boiling components and low-boiling components were removed by using two distillation columns (second distillation system), and a purified hexafluoro-1,3-butadiene (hereinafter called "purified product 1") was obtained. The purified product 3 was analyzed by gas chromatography to show that the hexafluoro-1,3-butadiene had a purity of 99.995% by volume or more. Low-boiling components were further removed by using another distillation column (third distillation system) to give a purified hexafluoro-1,3-butadiene (hereinafter called "purified product 2"). The purified product 2 was analyzed by gas chromatography to show that the hexafluoro-1,3-butadiene had a purity of 99.999% by volume or more.

Aftertreatment Step (Addition)

To 150 g of the reaction product residue obtained in the reaction step (the reaction product residue after separation by further heating to vaporize a part of the organic solvent and the product), 150 g of water and 2.5 g of 35% by mass hydrochloric acid were added, and the whole was stirred. The mixture was then filtered through a filter paper, type 5B, for quantitative analysis to remove insoluble substances, giving a filtrate.

After Treatment Step (Formation of Aqueous Zinc Chloride Solution)

The filtrate obtained in the aftertreatment step (addition) was subjected to simple distillation (fourth distillation system) to remove the organic solvent (2-propanol) by evaporation. Distillation was performed until the distillate fraction containing 2-propanol reached a total amount of 150 g, and then the distillation residue was collected to give an aqueous zinc chloride solution having a zinc chloride concentration of 51% by mass. The aqueous zinc chloride solution had a sufficiently, industrially valuable purity, which was shown by the following purity determination results.

Determination of Purity

The purity of the aqueous zinc chloride solution was determined by the following two methods.

Determination 2

The zinc in the aqueous zinc chloride solution was quantitatively determined by chelatometric titration using ethylenediaminetetraacetic acid (EDTA), and the result was converted into a zinc chloride amount. In the measurement, all zinc in the aqueous zinc chloride solution was assumed to be in the form of zinc chloride.
Next, the water in the aqueous zinc chloride solution was quantitatively determined by Karl Fischer method. The amount of the zinc chloride and the amount of the water were subtracted from the total amount of the aqueous zinc chloride solution to give the impurity amount in the aqueous zinc chloride solution. As a result, the impurity amount in the aqueous zinc chloride solution was less than the detection limit.

Determination 2

The aqueous zinc chloride solution was analyzed by gas chromatography. Only 832 ppm by mass of 2-propanol was quantitatively determined as the component other than zinc chloride or water. Diisopropyl ether and freons were detected as other impurities, but these amounts were too small for quantitative determination.

Example 2

Reaction Step

The step was the same as in Example 1.

Aftertreatment Step (Addition)

The step was the same as in Example 1.

Aftertreatment Step (Formation of Aqueous Zinc Chloride Solution)

The filtrate obtained in the aftertreatment step (addition) was distilled with a rotary evaporator to remove the organic solvent (2-propanol) by evaporation. Distillation was performed until the distillate fraction containing 2-propanol reached a total amount of 150 g, and then the distillation residue was collected to give an aqueous zinc chloride solution having a zinc chloride concentration of 48% by mass. The aqueous zinc chloride solution had a sufficiently, industrially valuable purity, which was shown by the following purity determination results.

Determination of Purity

The purity of the aqueous zinc chloride solution was determined in the same manner as in Example 1.

Determination 1

The impurity amount in the aqueous zinc chloride solution was less than the detection limit.

Determination 2

Only 1,002 ppm by mass of 2-propanol was quantitatively determined as the component other than zinc chloride or water. Diisopropyl ether and freons were detected as other impurities, but these amounts were too small for quantitative determination.

Example 3

Reaction Step

The step was the same as in Example 1.

Aftertreatment Step (Addition)

To 500 g of the reaction product residue obtained in the reaction step (the reaction product residue after separation by further heating to vaporize a part of the organic solvent and the product), 500 g of water and 1.0 g of 35% by mass hydrochloric acid were added, and the whole was stirred. The mixture was then filtered through a filter paper, type 5B, for quantitative analysis to remove insoluble substances, giving a filtrate.

Aftertreatment Step (Formation of Aqueous Zinc Chloride Solution)

The filtrate obtained in the aftertreatment step (addition) was distilled at a reflux ratio of 5:1 by using an Oldershaw type distillation apparatus having five trays to remove the organic solvent (2-propanol) by evaporation. Distillation was performed until the distillate fraction containing 2-propanol reached a total amount of 500 g, and then the distillation residue was collected to give an aqueous zinc chloride solution having a zinc chloride concentration of 49% by mass. The aqueous zinc chloride solution had a sufficiently, industrially valuable purity, which was shown by the following purity determination results.

Determination of Purity

The purity of the aqueous zinc chloride solution was determined in the same manner as in Example 1.

Determination 1

The impurity amount in the aqueous zinc chloride solution was less than the detection limit.

Determination 2

Only 486 ppm by mass of 2-propanol was quantitatively determined as the component other than zinc chloride or water. Diisopropyl ether and freons were detected as other impurities, but these amounts were too small for quantitative determination.

Comparative Example 1

Reaction Step

The step was the same as in Example 1.

Aftertreatment Step (Without Addition)

Through a filter paper, type 5B, for quantitative analysis, 150 g of the reaction product residue obtained in the reaction step (the reaction product residue after separation by further heating to vaporize a part of the organic solvent and the product) was filtered to remove insoluble substances, giving a filtrate.

Aftertreatment Step (Formation of Aqueous Zinc Chloride Solution)

The filtrate obtained in the aftertreatment step (without addition) was heated to evaporate the organic solvent (2-propanol), then solid substances were removed, and 75 g of water was added, giving an aqueous zinc chloride solution having a zinc chloride concentration of 45% by mass. The obtained aqueous zinc chloride solution contained large amounts of impurities and had a low industrial value, which was shown by the following purity determination results.

Determination of Purity

The purity of the aqueous zinc chloride solution was determined in the same manner as in Example 1.

Determination 1

The impurity amount in the aqueous zinc chloride solution was 5% by mass.

Comparative Example 2

Reaction Step

The step was the same as in Example 1.

Aftertreatment Step (Formation of Aqueous Zinc Chloride Solution Without Addition or Filtration)

First, 150 g of the reaction product residue obtained in the reaction step (the reaction product residue after separation by further heating to vaporize a part of the organic solvent and the product) was heated to evaporate the organic solvent (2-propanol), then solid substances were removed, and 75 g of water was added, giving an aqueous zinc chloride solution having a zinc chloride concentration of 45% by mass. The obtained aqueous zinc chloride solution contained large amounts of impurities and had a low industrial value, which was shown by the following purity determination results.

Determination of Purity

The purity of the aqueous zinc chloride solution was determined in the same manner as in Example 1.

Determination 1

The impurity amount in the aqueous zinc chloride solution was 5% by mass.

The invention claimed is:

1. A method for producing hexafluoro-1,3-butadiene, the method comprising:
   a reaction step of reacting a halogenated butane represented by chemical formula, $CF_2X^1$-$CFX^2$-$CFX^3$-$CF_2X^4$ ($X^1$, $X^2$, $X^3$, and $X^4$ are each independently a halogen atom other than a fluorine atom) in an organic solvent in the presence of zinc to eliminate the halogen atoms, $X^1$, $X^2$, $X^3$, and $X^4$, other than the fluorine atoms to generate hexafluoro-1,3-butadiene, giving a reaction product containing the hexafluoro-1,3-butadiene; and
   an aftertreatment step of separating the hexafluoro-1,3-butadiene from the reaction product produced in the reaction step, then adding water to a reaction product residue after the separating, wherein a mass ratio of the reaction product residue to the water ([amount of reaction product residue]/[amount of water]) is 0.5 or more and 2.0 or less, performing solid-liquid separation when a solution obtained by addition of water to the reaction product residue contains solid substances, and removing the organic solvent, giving an aqueous solution of zinc halide.

2. The method for producing hexafluoro-1,3-butadiene according to claim 1, wherein the organic solvent is an alcohol.

3. The method for producing hexafluoro-1,3-butadiene according to claim 2, wherein the alcohol is at least one of methanol, ethanol, 1-propanol, and 2-propanol.

4. The method for producing hexafluoro-1,3-butadiene according to claim 1, further comprising a neutralization step of bringing the hexafluoro-1,3-butadiene separated from the reaction product produced in the reaction step into contact with an alkali, and a water removal step of removing water from the hexafluoro-1,3-butadiene that has been brought into contact with the alkali in the neutralization step.

5. The method for producing hexafluoro-1,3-butadiene according to claim 4, further comprising a purification step of distilling the hexafluoro-1,3-butadiene from which water has been removed in the water removal step, by using at least two distillation columns to purify the hexafluoro-1,3-butadiene.

6. The method for producing hexafluoro-1,3-butadiene according to claim 1, wherein in the aftertreatment step, a hydrogen halide is added together with the water to the reaction product residue.

7. The method for producing hexafluoro-1,3-butadiene according to claim 2, further comprising a neutralization step of bringing the hexafluoro-1,3-butadiene separated from the reaction product produced in the reaction step into contact with an alkali, and a water removal step of removing water from the hexafluoro-1,3-butadiene that has been brought into contact with the alkali in the neutralization step.

8. The method for producing hexafluoro-1,3-butadiene according to claim 3, further comprising a neutralization step of bringing the hexafluoro-1,3-butadiene separated from the reaction product produced in the reaction step into contact with an alkali, and a water removal step of removing water from the hexafluoro-1,3-butadiene that has been brought into contact with the alkali in the neutralization step.

9. The method for producing hexafluoro-1,3-butadiene according to claim 2, wherein in the aftertreatment step, a hydrogen halide is added together with the water to the reaction product residue.

10. The method for producing hexafluoro-1,3-butadiene according to claim 3, wherein in the aftertreatment step, a hydrogen halide is added together with the water to the reaction product residue.

11. The method for producing hexafluoro-1,3-butadiene according to claim 4, wherein in the aftertreatment step, a hydrogen halide is added together with the water to the reaction product residue.

12. The method for producing hexafluoro-1,3-butadiene according to claim 5, wherein in the aftertreatment step, a hydrogen halide is added together with the water to the reaction product residue.

* * * * *